US006375970B1

(12) United States Patent
Bieniarz

(10) Patent No.: US 6,375,970 B1
(45) Date of Patent: Apr. 23, 2002

(54) METHODS AND MATERIALS FOR PRETERM BIRTH PREVENTION

(76) Inventor: Andre Bieniarz, 175 E. Delaware Ave., Ste. 7902, Chicago, IL (US) 60611

( * ) Notice: Subject to any disclaimer, the term of this patent is extended or adjusted under 35 U.S.C. 154(b) by 0 days.

(21) Appl. No.: 09/348,873

(22) Filed: Jul. 7, 1999

(51) Int. Cl.$^7$ ............................................ A61F 13/00
(52) U.S. Cl. .................... 424/422; 424/78.08; 428/500; 524/916; 604/48
(58) Field of Search ........................... 604/48; 424/422, 424/78.08; 428/500; 524/916

(56) References Cited

U.S. PATENT DOCUMENTS

| | | | |
|---|---|---|---|
| 4,188,951 A | 2/1980 | Higuchi et al. | 128/260 |
| 5,469,867 A | 11/1995 | Schmitt | 128/898 |
| 5,665,477 A * | 9/1997 | Meathrel et al. | 428/500 |
| 5,698,189 A | 12/1997 | Rowe et al. | 424/78.08 |
| 5,749,915 A | 5/1998 | Slepian | 623/1 |
| 5,779,673 A | 7/1998 | Roth et al. | 604/101 |
| 5,800,373 A | 9/1998 | Melanson et al. | 602/52 |
| 5,849,035 A | 12/1998 | Pathak et al. | 623/1 |
| 5,879,713 A | 3/1999 | Roth et al. | 424/489 |
| 5,900,245 A | 5/1999 | Sawhney et al. | 424/426 |
| 5,993,856 A * | 11/1999 | Ragavan et al. | 424/489 |

OTHER PUBLICATIONS

Akala, E.O. et al., "Novel pH–sensitive hydrogels with adjustable swelling kinetics," *Biomaterials, 19*:1037–1047 (1998).

Alleyne et al., "Efficacy and biocompatibility of a photopolymerized, synthetic, absorbable hydrogel as a dural sealant in a canine craniotomy model," *J. Neurosurg.*, 88:308–313 (1998).

Andreopoulos et al., "Release of Drugs from Polymeric Hydrogels," *J. Biomater. Appls.*, 12:291–99 (1998).

Anseth et al., "Mechanical properties of hydrogels and their experimental determination," *Biomaterials, 17*:1647–57 (1996).

Blanco et al., "Slow releasing of ara–C from poly(2–hydroxyethyl methacrylate) and poly(2–hydroxyethyl methacrylate–co–N–vinyl–2–pyrrolidone) hydrogels implanted subcutaneously in the back of rats," *Biomaterials, 19*:861–69 (1998).

Blue et al., "In Vivo Results of Hydrogel Composite Pericardial Substitutes," *ASAIO Transactions,* 37:M152–53 (1991).

Chetoni et al., "Silicone rubber/hydrogel composite ophthalmic inserts: preparation and preliminary in vitro/in vivo evaluation," *Eur. J. Pharm. Biopharm.*, 46:125–32 (1998).

Cifková et al., "Silicone rubber–hydrogel composites as polymeric biomaterials," *Biomaterials,* 11:393–396 (1990).

Corkhill et al., "Synthetic hydrogels VI. Hydrogel composites as wound dressings and implant materials," *Biomaterials, 10*:3–10 (1989).

Draye et al., "In vitro release characteristics of bioactive molecules from dextran dialdehyde cross–linked gelatin hydrogel films," *Biomaterials,* 19:99–107 (1998).

Gomez et al., "Poly(acrylaminde–co–monoethyl Itaconate) Hydrogels as Devices for Cytarabine Release in Rats," *J. Pharm. Pharmacol.* 50:703–712 (1998).

Hoffman, "'Intelligent' Polymers in Medicine and Biotechnology," *Artificial Organs,* 19(5):458–467 (1995).

(List continued on next page.)

Primary Examiner—Thurman K. Page
Assistant Examiner—Liliana Di Nola-Baron
(74) Attorney, Agent, or Firm—Marshall, Gerstein, & Borun

(57) ABSTRACT

Materials and methods for reducing the incidence of preterm birth involving the use of polymeric compositions are provided.

21 Claims, 8 Drawing Sheets

OTHER PUBLICATIONS

Hong et al., "Comparison of bone regeneration in a rabbit skull defect by recombinant human BMP–2 incorporated in biodegradable hydrogel and in solution," *J. Biomater. Sci. Polym. Ed., 9*(9):1001–1014 (1998).

Horák et al., "Hydrogels in endovascular embolization," *Biomaterials, 9*:367–371 (1988).

Iza et al., "Hydrogels of poly(ethylene glycol): mechanical characterization and release of a model drug," *J. Controlled Release, 52*:41–51 (1998).

Kikkinides et al., "A two–phase model for controlled drug release from biphasic polymer hydrogels," *J. Controlled Release, 51*:313–325 (1998).

Lopour et al., "Silicone rubber–hydrogel composites as polymeric biomaterials," *Biomaterials,* 11:397–402 (1990).

Martin et al., "Highly swelling hydrogels from ordered galactose–based polyacrylates," *Biomaterials, 19*:69–76 (1998).

Merrill et al., Partitioning and diffusion of solutes in hydrogels of poly(ethylene oxide) *Biomaterials, 14*(15):1117–26 (1993).

Nakayama et al., "Surface Fixation of Hydrogels Heparin and Glucose Oxidase Hydrogelated Surfaces," *ASAIO Journal,* 38:M421–24 (1992).

Oxley et al., "Macroporous hydrogels for biomedical applications: methodology and morphology," *Biomaterials, 14*:1064–72 (1993).

Ranger et al., "Pneumostasis of Experimental Air Links with a New Photopolymerized Synthetic Tissue Sealant," *Am. Surg., 63*(9):788–795 (Sep., 1997).

Slepian et al., "Polymeric Endoluminal Gel Paving: Therapeutic Hydrogel Barriers and Sustained Drug Delivery Depots for Local Arterial Wall Biomanipulation," *Semin. Intervent. Cardiol., 1*:103–16 (1996).

Slepian, "Polymeric Endoluminal Paving and Sealing: Therapeutic at the Crossroad of Biomechanics and Pharmacology," Section IV, Chapter 32, pp. 647–670.

Suggs et al., "Preparation and characterization of poly(propylene fumarate–co–ethylene glycol) hydrogels," *J. Biomater. Sci. Polym. Edn., 9*(7):653–66 (1998).

Tabata et al., "Bone regeneration by basic fibroblast growth factor complexed with biodegradable hydrogels," *Biomaterials, 19*807–815 (1998).

Tay et al., "Activity toward thrombin–antithrombin of heparin immobilized on two hydrogels," *Biomaterials, 10*:11–15 (1989).

Trigo et al., "Anticancer drug, ara–C, release from pHEMA hydrogels," *Biomaterials, 15*(14):1181–86 (1994).

Watler et al., "Water content and compression modulus of some heparin–PVA hydrogels," *Biomaterials, 9*:150–54 (1988).

Yamamoto et al., "Ectopic bone formation induced by biodegradable hydrogels incorporating bone morphogenetic protein," *J. Biomater. Sci. Polymer Edn., 9*(5):439–458 (1998).

* cited by examiner

METHODS AND MATERIALS FOR PRETERM BIRTH PREVENTION

FIELD OF THE INVENTION

The present invention relates generally to the intrauterine use of compliant polymeric substances in pregnant women to reduce the incidence of preterm birth comprising polymeric compositions selected for ability to prevent amniotic fluid leakage in cases of ruptured amniotic membranes and to provide a physical cervical barrier to migration of microbes, and optionally for ability to release therapeutic agents to prevent labor and/or infection.

BACKGROUND OF THE INVENTION

In the United States, approximately 300,000 newborns are born prematurely every year, a figure that represents about 6% to 10% of all newborns. Preterm premature rupture of fetal membranes (PROM) is a factor in a majority of these births. About 20% of these premature infants die in the first month. Survivors may suffer short or long term morbidity involving every organ system. The hospitalization costs of the acute antepartum maternal care, the neonatal intensive care and the immediate care of the prematurely born infant, are enormous and often exceed $500,000 per case. Additional costs for care of the premature newborn continue to accrue after discharge from the hospital and potentially throughout the child's life, including further care due to life long handicaps and the cost of lost productivity due to these handicaps.

The cause of premature labor or rupture of the fetal membranes is almost certainly multifactorial. One factor leading to PROM is breach of the cervical barrier that separates the vagina, which is colonized by a multitude of microbial families, from the sterile intrauterine environment. Such a breach of the cervical barrier can be due to the virulence of a given bacterial population or to deficits in immune or biochemical mechanisms that control the advance of microbes through the cervical canal. Alternatively, or concurrently, mechanical defects due to structural uterine or cervical abnormalities or prematurely occurring biochemical changes in the cervical tissue which lead to the premature opening of the cervical canal can cause or contribute to the process which ultimately culminates in PROM.

Two fundamental physiological processes in the uterine corpus and cervix are required for premature expulsion of the fetus to occur. In the uterine corpus (the body of the uterus), the muscular myometrium must change from a relaxed state, which is crucial to the continuation of pregnancy, to a state characterized by a rhythmic contractile activity that culminates in the expulsion of the products of conception. Meanwhile, the cervix must gradually yield, soften, efface and dilate. The softened and dilated cervix can no longer support the fetal chorioamniotic membranes, and eventually the membranes stretch and balloon through the cervical opening into the vagina. Occasionally, this ballooning action overcomes the tensile strength of the chorioamniotic membranes and leads to their rupture. Additionally, cervical softening and dilatation may allow the access of microbes into the lower uterine segment.

There are three main structural components of the cervix: smooth muscle, collagen, and the connective tissue "ground substance". The last is composed of the cervical glycosaminoglycans such as dermatan sulfate, chondroitin sulfate, and hyaluronic acid. Changes that take place in the collagen and in the connective tissue matrix of the cervix appear to be the primary factors allowing the cervix to soften and open in both normal and preterm labor. During pregnancy, dermatan and chondroitin sulfates bind tightly to collagen fibers and secure them in a dense collagen framework that ensures that the cervix remains firm and closed during normal pregnancy. The hyaluronic acid content is believed to play a role in the water retention capacity of the cervical tissue. At the end of pregnancy (or in events leading to premature labor), the cervical structure is completely remodeled so that it becomes soft and easily distensible. Collagen degradation becomes predominant as collagenase and other associated enzymes are activated and cervical dermatan sulfate concentrations diminish, causing disruption of the collagen framework and cervical matrix. The breakdown and loss of collagen and dermatan/chondroitin sulfates increase the flexibility and distensibility of the cervix, while the cervix also becomes swollen, soft and fragile due to increased hyaluronic acid and water content.(8)

With progressive softening, flexibility and distensibility of the cervical tissue, the mechanical support for the overlying chorioamniotic membranes gradually fails, leading to stretching of the fetal membranes in response to uterine activity and an increased risk of PROM. Mechanical stretching of the fetal membranes up-regulates the production of several amniotic factors, including prostaglandin E2 and interleukin-8. Stretch also increases the interstitial collagenases and matrix metalloproteinase- 1 (MMP- 1) within the membranes. (8) Prostaglandin E2 increases uterine irritability, decreases fetal membrane collagen, and increases production of MMP- 1 by human fibroblasts. (9,10) Interleukin-8, which is produced by amniotic and chorionic cells, is chemotactic for neutrophils and stimulates collagenase activity. The production of interleukin-8, which is present in low concentration in the amniotic fluid during the normal second trimester but in much higher concentrations late in gestation, is inhibited by progesterone. These processes leading to the PROM represent an acceleration or exaggeration of normal physiologic process, which in the normal pregnancy lead to a spontaneous rupture of membranes during labor.

There is indirect evidence that genital tract infection precipitates rupture of the membranes in animals and humans. In pregnant rabbits, cervical inoculation with *Escherichia coil* resulted in positive cultures for *E. coli* in the amniotic fluid and decidual tissue of ninety-seven percent of the treated animals and preterm delivery in half of the treated animals, while cervical inoculation of saline in control animals resulted in no infections or preterm births. (11) The identification of pathologic microorganisms in human vaginal flora soon after membrane rupture also support the idea that bacterial infection plays a role in the pathogenesis of premature membrane rupture. (12) Epidemiologic data demonstrate an association between colonization of the genital tract with group B streptococci, *Chlamydia trachomatis, Neisseria gonorrhoeae*, and the microorganisms that cause bacterial vaginosis and an increased risk of preterm premature rupture of the membranes. (13, 14).

Intrauterine infection may predispose women to rupture of the fetal membranes through any of several potential mechanisms, each of which induces degradation of the extracellular matrix. Proteases secreted by vaginal microbes can degrade collagen and weaken the fetal membranes. The host inflammatory response to bacterial infection, which is mediated by polymorphonuclear neutrophils and macrophages that are recruited to the site of infection, causes production of cytokines, matrix metalloproteinases, and prostaglandins. These substances further decrease the tissue support and the tensile strength of fetal membranes and also increase uterine activity, all of which contribute to the eventual rupture of the membranes.

Approximately 70% of premature births occur after PROM or pre-term labor (17). In spite of major advances in the fields of neonatal and perinatal medicine the outcome of PROM in the second or early third trimester is still associated with high mortality and morbidity. A major contributor to these sub-optimal outcomes following PROM is oligohydramnios (an inadequate amount of amniotic fluid surrounding the fetus). Oligohydramnios is a factor in perinatal asphyxia, chorioamnionitis, abruptio placenta, hypoplastic fetal lung, fetal compression abnormalities and amniotic band formation. The gestational age at which the rupture of membranes occurs and the persistence of oligohydramnios after PROM have a profound influence on perinatal outcome. The perinatal mortality rate in cases with documented rupture of membranes before 26 weeks of gestation, managed expectantly with bed rest, was recently reported to be 78.3%, while the perinatal mortality for newborns delivered at or beyond 26 weeks gestation was reported at 33.3%. (18).

The optimum management of PROM is not established but involves balancing the risks of active intervention (delivery) against watchful expectancy until fetal maturity or decompensation is documented. Recent clinical studies of PROM have documented that the risks of perinatal death from prematurity exceed the risks of infection from delayed delivery after PROM (23–26). Thus, expectant management is presently advocated by the overwhelming majority of perinatologists (27). However, attempts to manage patients with PROM in mid trimester have so far met with minimal success (18, 28–30). To successfully manage PROM, the problems of uterine contractions, infection and oligohydramnios, which are the chief contributors to perinatal mortality and morbidity, must be addressed. Present clinical management of PROM (18, 28–30) addresses the problem of uterine contractions by administering tocolytic therapy. However, the problems of infection and amniotic fluid leakage are not usually actively addressed. Patients are usually monitored for the development of these two complications of PROM without any attempts to prevent or actively treat these problems other than inducing delivery of the fetus.

Three clinical experience reports have described attempts to use fibrin glue to prevent leakage of amniotic fluid after PROM (31–33). Fibrin glue is composed of two components—fibrinogen and thrombin. When mixed together, the clotting cascade is initiated to form a fibrin clot or plug. Fibrin glue has been used widely in Europe since 1970 as a tissue sealant and hemostatic agent. Its use was mostly confined to trauma and surgical emergency situations where acute hemostatic control or cerebrospinal fluid leakage control was necessary. However, the glue was prepared commercially from pooled human blood and consequently carried a risk of hepatitis and HIV infections. In 1978 the Food and Drug Administration banned the use of commercially available fibrin glue because of its pooled human fibrinogen origin. Fibrin glue prepared from a patient's own plasma may still be used in non-emergency situations when there is time to prepare the glue.

Although the fibrin glue sealing procedure was reported to be successful in patients with PROM, the total number of patients involved was very small and the results were not compared to control groups treated with standard therapy. Thus, the clinical usefulness of fibrin glue sealing in PROM, in terms of providing prolonged gestation and decreased perinatal morbidity and mortality, remains unproven. In addition, the procedure has several significant disadvantages and limitations. The process of preparing fibrin glue from autologous plasma is long and cumbersome and requires that the patient self-donate plasma and be back-transfused with her own red blood cells. The bonding and strength properties of such autologous fibrin glue vary widely among patients because the level of fibrinogen, the main component of the glue, varies among patients. The mechanical properties of the fibrin plug provide neither adequate physical support to the tissues nor a significant barrier to bacteria. The fibrin glue will also promptly lose effectiveness as it is degraded by the patient's own enzymes. The rate of degradation varies greatly due to differences in fibrinolytic activity among each patient and thus makes it difficult to predict the length of time that the fibrin glue will remain effective as a sealant and also makes it almost impossible to determine an appropriate amount of potential additives, such as antibiotics or antithrombolytics, that might be incorporated into the glue. Finally, the almost instantaneous clotting of the fibrin glue upon contact of the fibrinogen and thrombin components limits the ability to tailor the shape of the fibrin glue plug (for example, to flow into uneven surface interstices and also to be shaped for optimal structural support for the chorioamniotic membranes and the lower uterine segment and internal cervical os) and renders the fibrin glue plug non-homogeneous in its composition and strength. In view of these limitations, autologous fibrin glue is not a wholly satisfactory substance for sealing of prematurely ruptured chorioamniotic membranes.

Thus, a need continues to exist for methods and devices or systems that reduce the incidence of preterm delivery, for example, by preventing the vaginal leakage of amniotic fluid after PROM, by providing local mechanical support to the cervix and fetal membranes, or by establishing a physical barrier to the passage of the bacteria from the vagina to the lower uterine segment and fetal membranes. A need also exists for a local pharmacological agent delivery system. Ideally, such methods and devices or systems would not require the patient to be confined in a hospital.

Of interest to the present invention are reports that hydrogels have been used for sealing of tissue [see, e.g., U.S. Pat. Nos. 5,900,245 or 5,800,373], in pleural or dural repair [Lyman et al., *Ann. Biomat.*, 2:212 (1996); Alleyne et al., *J. Neurosurg.*, 88:308–313 (1998)], in endoluminal gel paving of blood vessels [see, e.g., U.S. Pat. No. 5,749,915 and Slepian et al., *Semin. Interv. Cardiol.*, 1: 103–16 (1996)], in pericardial patches [Blue et al., *ASAIO Transactions*, 37:M152–53 (1991)] and as wound dressings and implants [Corkhill et al., *Biomaterials*, 10:3–10 (1989)]. Also of interest is a report that heated flowable polymers may be used to occlude channels in mammalian tissue [U.S. Pat. No. 5,469,867].

Of further interest are reports that hydrogels or other polymers may be used to release biologically active agents [see, e.g., U.S. Pat. No. 5,879,713; Martin et al., *Biomaterials*, 19:69–76 (1998)], including intrauterine delivery of drugs [U.S. Pat. No. 4,188,951], delivery of basic fibroblast growth factor to skull bone [Tabata et al., *Biomaterials*, 19:807–815 (1998)], delivery of bone morphogenetic protein-2 (BMP-2) to skull bone [Hong et al., *J. Biomater. Sci. Polym. Ed.*, 9:1001–1014 (1998)], release of cytarabine (ara-C) to plasma from back implants [Blanco et al., *Biomaterials*, 19:861–69 (1998); Gomez et al., *J. Pharm. Pharmacol* 50:703–712 (1998)], release of epidermal growth factor [Draye et al., *Biomaterials*, 19:99–107 (1998)], release of heparin [Nakayama et al., *ASAIO*

Journal, 38:M421–24 (1992)] and delivery of antibiotics to the eye [Chetoni et al., *Eur. J. Pharm. Biopharm.*, 46:125–32 (1998)].

Also of interest are studies of the mechanical properties of hydrogels [Suggs et al., *J. Biomater. Sci. Polym. Ed.*, 9:653–66 (1998); Anseth et al., *Biomaterials*, 17:1647–57 (1996); Oxley et al., *Biomaterials*, 14:1064–72 (1993); Watler et al., *Biomaterials*, 9:150–54 (1988)] and studies of the diffusion and release properties of hydrogels [see, e.g., Iza et al., *J. Controlled Release*, 52:41–51 (1998); Kikkinides et al., *J. Controlled Release*, 51:313–325 (1998); Andreopoulos et al., *J. Biomater. Appl.*, 12:291–99 (1998); Merrill et al., *Biomaterials*, 14:1117–26 (1993); Trigo et al., *Biomaterials*, 15:1181–86 (1994)] and hydrogel composites [Cifkova et al., *Biomaterials*, 11:393–396 (1990), Lopour et al., *Biomaterials*, 11:397–402 (1990)].

SUMMARY OF THE INVENTION

The present invention provides a uterine cervix and intrauterine polymeric system on (adjacent to) chorioamniotic membrane comprising a first polymeric material. This first polymeric material may be adherent to the chorioamniotic membrane, may have an elongation at rupture similar to or greater than that of chorioamniotic membrane, or may be characterized by an elongation at rupture, elastic modulus, tensile stress and tensile modulus that provides sufficient physical support to reduce stretching of the chorioamniotic membrane into (or through) the uterine cervix during pregnancy. Preferably, the force required to rupture said first polymeric material is similar to or greater than that required to rupture chorioamniotic membrane. The first polymeric material may also form a physical barrier preventing migration of vaginal microbes into the uterus.

The first polymeric material is preferably a hydrogel. The polymeric material may further comprise a second polymeric composition located intracervically, and optionally may further comprise a third polymeric composition located in the vaginal portion of the cervix. The second and third polymeric compositions may be the same as or different from the first polymeric material.

The first, second or third polymeric compositions can release therapeutic amounts of pharmaceutical agents into the uterine and cervical area over a time period selected from the group consisting of 1 day, 2 days, 3 days, 1 week, 2 weeks, 3 weeks, and 4 weeks or more. For example, drug release may be provided by incorporation of microspheres comprising a pharmaceutical agent into said polymeric compositions. Suitable pharmaceutical agents include antibiotics, labor-inhibiting agents, tocolytic agents, prostaglandin inhibitors, anti-inflammatory agents, anti-proteolytic agents, estrogenic agents, progestogenic agents, steroid hormones, and any other substance beneficial to prolonging gestation.

The invention also provides methods for forming the polymeric material (system) of claim 1 comprising the steps of: contacting the lower uterine segment with a polymerizable solution and polymerizing said material to form said system, optionally further comprising the steps of administering a polymerizable composition into the cervix of a pregnant female, and polymerizing said composition.

Methods of the invention include methods for reducing the incidence of preterm birth comprising the steps of administering a polymerizable composition into the lower uterine segment of the uterus of a pregnant female, and polymerizing said composition. According to such methods, pregnancy is prolonged and preterm labor and birth is prevented. Females to be treated include females suffering from premature labor, suffering from premature rupture of fetal chorioamniotic membrane (PROM), and females at risk of preterm labor. Signs of risk of preterm labor include high levels of oncofetal fibronectin, documented high proteolytic activity, signs of cervical softening or ripening, a significantly shorter cervix, a prior history of cervical incompetence, cervical funneling, a prior history of preterm birth, and a prior history of PROM.

Numerous additional aspects and advantages of the invention will become apparent to those skilled in the art upon consideration of the following detailed description of the invention which describes presently preferred embodiments thereof.

DETAILED DESCRIPTION OF THE INVENTION

Figure 1:
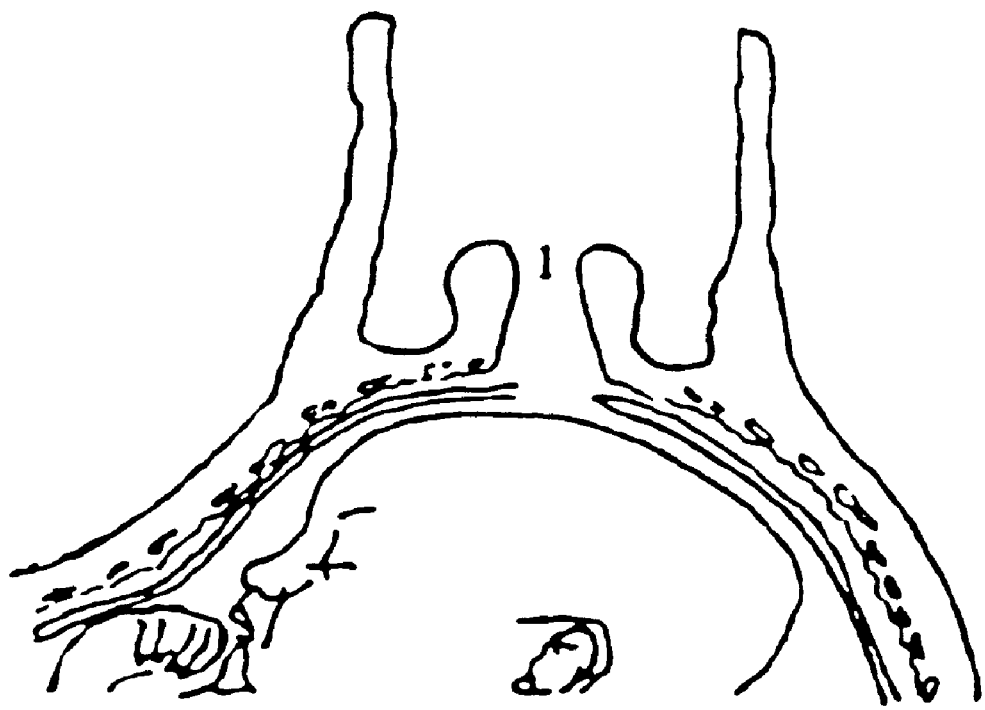
FIGS. 1 through 8 illustrate steps of one exemplary protocol for applying polymerizable solutions to the lower uterine segment and cervix.

One aspect of the present invention provides methods for using a polymeric composition in a female to provide physical support to the cervix and lower uterine segment. In a pregnant female, the methods may also be used to provide support to fetal membranes and to prevent amniotic fluid leakage in cases of ruptured fetal membranes, and is expected to result in reduced incidence of preterm birth and reduced incidence of intrauterine infection.

Subjects that may be treated, both therapeutically and prophylactically, according to the methods of the invention include pregnant women suffering from preterm labor, or preterm rupture of fetal amniotic membranes or at risk of preterm labor or ruptured membranes. Females at risk of preterm premature birth include females with high levels of oncofetal fibronectin, with a significantly shorter cervix (diagnosed, e.g., by ultrasound), with documented high proteolytic activity, or with other signs of pre-term cervical softening or ripening, with prior cervical incompetence, with cervical funneling, with a prior history of preterm birth, with a prior history of preterm premature rupture of fetal membranes, or with other risk factors or conditions that predispose the pregnant female to preterm premature birth.

According to the methods of the present invention, a composition of the desired properties may be infused and polymerized in the lower uterine segment to provide physical support to the fetal membranes and to the surrounding tissues, and may even be used to seal ruptured fetal membranes. Subsequently, and if appropriate in the clinical situation, a similar or a different composition may be infused and polymerized in the cervical canal, and may be used to provide a barrier to ascent of microbes from the vagina to the uterus. Finally, if indicated, a poorly compliant but mechanically stronger polymeric mold may be formed in the vagina and may be secured to the external, vaginal portion of the cervix at a predetermined location to provide resistance to opening of the cervix, which could result in the loss of the fetus. The subject is monitored over time, and if desired, a further composition(s) may be infused and polymerized.

The methods of the present invention may also include local delivery of one or more beneficial therapeutic agents to the uterus, including uterine muscle, fetal membranes and amniotic fluid, and/or to the cervix in order to prevent labor and/or infection, either via the first polymeric supporting composition or via a second polymeric composition adjacent to or incorporated within the first polymeric supporting composition. The polymeric compositions may allow for time-released delivery of the therapeutic agents, possibly over a long period of time of 1, 2, 3, 4 weeks or more.

Suitable therapeutic agents may, for example, decrease collagenolysis, proteolysis, interleukin and prostaglandin production in the lower uterine segment by inhibiting the effect of collagenases, proteases, interleukins or prostaglandins or by interfering with local production of these substances. Classes of suitable therapeutic agents include labor-inhibiting therapeutic agents, antibiotics, tocolytic agents, anti-inflammatory agents, anti-proteolytic agents, steroid hormones, other agents that inhibit the physiological and biochemical processes leading to delivery, and other pharmaceutical products appropriate for local delivery to the cervical, uterine and fetal membrane tissues.

A second aspect of the invention provides an intrauterine or transcervical supporting and/or sealing system (or device) formed within the lower uterine segment of a pregnant woman comprising at least one polymeric supporting composition. This system (device) may extend from the lower uterine segment into the cervical canal, and may optionally be secured to the external, vaginal portion of the cervix and may even extend into the vagina. The system may take the form of a lower uterine or cervical polymeric plug. The properties of the polymeric compositions can vary at different locations within the system. For example, there may be differences among the portions located in the lower uterine segment, the cervix and the vaginal portion of the cervix. The polymeric composition used for physical support is preferably a polymeric composition selected for physical or mechanical properties that provide physical support to the cervix, lower uterine segment and fetal membranes. The same or further polymeric compositions may also prevent amniotic fluid leakage when fetal membranes are ruptured and may provide a physical barrier to the movement of microbes from the vagina to the lower uterine segment. To achieve this purpose, the polymeric composition can be formulated to demonstrate a high initial tack, be bacteriostatic, and have bond strength that is not altered by the presence of moisture. The polymeric composition may provide physical support sufficient to reduce stretching of the chorioamniotic membrane into (or through) the uterine cervix during pregnancy, which can be indicated, for example, by maintenance or improvement of the patient's clinical condition, prolongation of gestation, and/or returning the cervix to a closer to normal configuration (including maintenance of cervical length or reduction in cervical funneling).

The supporting and/or sealing system consists of a polymeric material or materials which are substantially completely inert and harmless to, or biocompatible with, the surrounding body tissues. Such material(s) most preferably will not provoke an immune response. The material(s) may be biodegradable or may remain substantially unabsorbed by the human body. A large variety of polymeric materials are known in the art and include materials such as described in U.S. Pat. Nos. 5,900,245 or 5,469,867, both of which are incorporated herein by reference, and hydrogels or other homopolymers or copolymers composed of, e.g., polyethylene glycol [Isa et al., supra, incorporated herein by reference] or other alkylene glycol; polypropylene fumarate [Suggs et al., supra, incorporated herein by reference, describing block copolymers composed of polypropylene fumarate and polyethylene glycol]; galactose [Martin et al., supra, incorporated herein by reference, describing acylation of beta-O-methyl-galactopyranoside]; gelatin [Draye et al., supra, incorporated herein by reference, describing cross-linking of gelatin with dextran dialdehydes and Hong et al., supra, incorporated herein by reference]; and acrylic acid [Blanco et al., supra, incorporated herein by reference, and Andreopoulous et al., supra, incorporated herein by reference, describing poly(2-hydroxyethyl methacrylate) and poly(2-hydroxyethyl methacrylate-co-N-vinyl-2-pyrrolidone crosslinked with ethylene glycol dimethacrylate); Chetoni et al., supra, incorporated herein by reference, describing a polyacrylic acid or polymethacrylic acid polymer network; Akala et al., *Biomaterials,* 19:1037–47 (1998), incorporated herein by reference, describing copolymerization of N,N-dimethylacrylamide, tert.-butylacrylamide, acrylic acid, 4,4'-di(methacryloylamino)azobenzene, and N-alkanoyl, O-methacryloylhydroxylamines], including copolymers of acrylic acid and acrylic acid salts, copolymers of acrylic acid and esters derived from alcohol amines, copolymers of acrylic acid and vinyl pyrrolidone, and copolymers of acrylic acid and acrylates. Silicone rubber-hydrogel composites are also known in the art [see Cifkova et al., supra, incorporated herein by reference]. See Corkhill et al., supra, incorporated herein by reference, for a review of further varieties of hydrogel biomaterials.

Hydrogels are biocompatible and biodegradable and are preferred in the methods and systems of the present invention. They are formed by polymerization of a solution which can be administered in vivo into body cavities and polymerized within a very short time frame. Appropriate selection of hydrogel components permits rapid, controlled polymerization and gelation, in aqueous surrounds, using a variety of initiating systems such as heat, visible light, ultraviolet light, electron beam, redox reagents, changes in hydrogen ion concentration and other initiators. For example, Suggs et al., supra, incorporated herein by reference, report that the mechanical properties of cross-linked polypropylene fumarate-co-ethylene glycol, including swelling ratios, elastic moduli, tensile stresses and tensile moduli, depend on polyethylene glycol (PEG) content, polypropylene fumarate (PPF) content and PPF molecular weight. Suggs et al. determined that increasing the molecular weight of PPF or of PEG increases the elastic moduli and reduces compliance. Increasing the weight percent of PEG increases compliance, while increasing the relative amount of PPF decreases compliance. Tensile stress and moduli increase with increasing PPF molecular weight and decrease with increasing PEG content. [See also Oxley et al., supra, and Watley et al., supra, both of which are incorporated herein by reference.] Precisely conforming, biocompatible and biodegradable structures tailored to the intrauterine or intracervical area to be sealed can be formed in vivo and the physical or mechanical properties of the polymeric composition can be selected for desired strength and compliance.

An exemplary sealant formulation according to the present invention consists of the following composition polymerized by exposure to ultraviolet radiation:

| | |
|---|---|
| Water | 10.7% |
| Acrylic acid | 21.7% |
| 2-hydroxy-2-methyl-1-phenyl-propane-1-one (photoinitator; DAROCUR ™ 1173; Ciba Geigy) | 0.33% |
| Polyethylene glycol (400) Diacrylate (crosslinking agent; SARTOMER ™ 344; Sartomer Co., Westchester, PA) | 0.17% |
| Glycerine | 27.8% |

-continued

| | |
|---|---|
| (humectant and plasticizer providing dry tack properties) Colloid 121 (polyacrylic acid solution enhancing wet tack, viscosity and formability properties; Rhone Poulenc, Marieta, GA) | 14.9% |
| Diisopropanolamine (humectant and plasticizer, helps to neutralize acid and provides good wet adhesive properties) | 13.8% |
| Potassium chloride | 1% |
| Aqueous sodium hydroxide 27% | 0.96% |

The intrauterine or intracervical supporting and/or sealing device or system may optionally also comprise a drug delivery system. The polymeric composition used for drug administration is selected for diffusion or release properties that allow controlled release of therapeutic agents to prevent labor and/or infection, and may be the same polymeric supporting composition used for physical support or a second, different polymeric delivery composition. The therapeutic agent may be incorporated directly into the polymeric supporting composition or may be encapsulated in microparticles such as liposomes, microspheres or microcapsules. Any suitable polymeric compositions or polymeric matrices incorporating microparticles known in the art may be used, such as hydrogels, organogels, and films, including those described in U.S. Pat. No. 5,879,713, incorporated by reference herein. A variety of materials suitable for drug release are known in the art and include those described in Martin et al., supra, U.S. Pat. No. 4,188,951, Tabata et al., supra, Hong et al., supra, Blanco et al., supra, Gomez et al., supra, Draye et al., supra, Nakayama et al., supra, Chetoni et al., supra, Iza et al., supra, Kikkinides et al., supra, Andreopoulos et al., supra, Merrill et al., supra, Trigo et al., supra, Cifkova et al., supra, and Lopour et al., supra, all of which are incorporated herein by reference. Hydrogels are a preferred material for controlled drug delivery. Release of the therapeutic agent from the hydrogel can occur by diffusion and/or by release of the agent from the polymer as it degrades. The polymeric delivery composition can also be used for drug delivery to the vagina, cervix, uterus and ovaries in the non-pregnant state.

The system may be composed of multiple parts, for example, located in the lower uterine segment, the cervix and the vaginal portion of the cervix. Each part may incorporate one or multiple therapeutic agents that may be different from the therapeutic agents contained in the other parts of the system. Thus, the lower uterine segment portion might be used to concurrently deliver anti-inflammatory agents, antibiotics and tocolytics selected to prevent contraction of the myometrium, while the cervical segment of the system might contain antibiotics and steroid hormones selected to decrease collagenolysis and to reform cervical ground substance.

The optimum formulation for purposes of sealing chorioamniotic membranes and/or drug delivery to the uterus and cervix can be established by assays known in the art. For example, the in vitro or in vivo models described in Examples 1 and 2 below can be used to determine suitability for sealing ruptured membranes. Procedures known in the art for measuring drug diffusion and/or release in vitro or in vivo, including those described in the art cited herein, all of which is incorporated herein by reference, can be used to determine suitability for drug delivery.

Any devices or methods known in the art may be used to assist in forming the intrauterine polymeric barrier system of the invention, including those described in U.S. Pat. Nos. 5,900,245, 5,800,373, 5,879,713, 5,779,673, 5,849,035, 5,749,915 and 5,698,189, all of which are incorporated herein by reference.

The methods and materials of the present invention provide the following advantages: (1) providing physical and structural support to the cervix, including the vaginal portion of the cervix, (2) providing physical and structural support to the lower uterine segment; (3) providing physical-structural support to the fetal membranes; (4) providing a barrier to passage of bacteria or other infectious or noxious entities from the vagina into the lower uterine segment; (5) drug delivery to the vagina; (6) drug delivery to the vaginal portion of the cervix; (7) drug delivery to the cervical canal; (8) drug delivery to the internal os of the cervix and to the uterus; (9) sealing the rent in the fetal membranes.

The methods and materials of the present invention are expected to significantly decrease immediate hospital care costs and drastically improve patient comfort. Sealing of the rent in chorioamniotic membranes or placement of a barrier at the internal cervical os and possibly in the cervical canal is also expected to prevent amniotic fluid leakage and significantly decrease the fetal risks associated with oligohydramnios, including the risk of chorioamnionitis, stillbirths, malpresentation, low Apgar scores, cord accidents, fetal distress, spontaneous placental separation or abruptio placenta, pulmonary hypoplasia, perinatal asphyxia, fetal compression abnormalities and amniotic band formation, and other adverse outcomes, including neonatal infection, intraventricular hemorrhage, necrotizing enterocolitis, and respiratory distress syndrome. The barrier to microbial ascent into the uterus, together with the local delivery of antibiotics, is also expected to reduce the incidence of infection which is an important risk factor for premature delivery. Finally, the physical support provided to the lower uterine segment, cervix and fetal membranes, together with local delivery of anti-inflammatory and antiproteolytic agents, is expected to reduce the softening of the cervix which is another important risk factor for premature delivery. The end result of these effects is expected to be the prolongation of gestation, prolongation of latent period (length of time from premature rupture of membranes to delivery time), reduction in incidence of preterm birth, a reduction in intrauterine infection, and a reduction in maternal and neonatal morbidity and mortality.

Other aspects and advantages of the present invention will be understood upon consideration of the following illustrative examples. Example 1 addresses use of a hydrogel composition to seal ruptured fetal membranes in vitro. Example 2 addresses use of a hydrogel composition to seal ruptured fetal membranes in baboons.

EXAMPLE 1

Sealing of ruptured fetal amniotic membranes in vitro

Two polymeric support compositions were tested for ability to bind to freshly harvested human fetal membranes and ability to seal an artificially created hole in the fetal membranes in vitro. One composition of lower viscosity (LVPS) and one composition of higher viscosity (HVPS) [both LVPS and HVPS were a Focal Seal Gel from Focal, Lexington, Mass.] were tested. Both LVPS and HVPS were composed of two parts—primer and sealant. The primer component is applied initially and is immediately followed by the application of the sealant component. The mixture of the primer and the sealant is treated with visible light, which is focused on the compound by a fiberoptic wand, to initiate polymerization. LVPS has a viscosity similar to that of honey while HVPS is slightly more viscous and beads on the surface it is applied to with minimal to no runoff.

Initial experiments evaluated the binding of LVPS and HVPS to the fetal membranes by four different techniques for each polymeric composition:

a. The primer component was brushed on the fetal membrane surface followed by dripping the sealant onto the fetal membrane and finally treating (polymerizing) the mixture with visible light concentrated through a fiberoptic wand;

b. The primer was dripped onto the fetal membrane followed by dripping the sealant and treating with light from a fiberoptic wand;

c. The sealant was dripped onto the fetal membrane, without pre-treating the surface with the primer, followed by treating with light from a fiberoptic wand; and d. The primer was dripped onto the fetal membrane followed by dripping the sealant, without treatment with light from a fiberoptic wand (although some visible light was present in the room).

The strength of the binding binding of the LVPS or HVPS to the fetal membranes was tested by grasping the edge of the polymerized (cured) compound with a forceps attached to a dynamometer and attempting to lift the compound off of the fetal membrane surface.

The results demonstrated adequate binding of LVPS and HVPS to the fetal membranes in all experiments using all four techniques (a–d) described above. The (a) and (b) techniques were judged to produce better binding than the (c) and (d) techniques. Even though approach (a), brushing the primer onto the fetal membrane, appeared to result in marginally better binding than approach (b), where both the primer and the sealant were dripped onto the membrane surface, this difference appeared to be minor. Both approaches (a) and (b) resulted in binding powerful enough that forcing the polymer off the fetal membrane resulted in the separation of the chorion and amnion layers of the membrane before the dehiscence of the polymer. Parts of the chorion remained attached to the polymer after its forceful removal from the site of application. The significance of this finding is that brushing the primer component onto the surface of the fetal membrane, which would be technically extremely difficult in the lower uterine segment, does not appear to be essential to achieve strong binding.

Only marginal differences in binding performance could be observed between LVPS and HVPS. The polymers forcefully separated from the membrane were inspected. They had a consistency of gelatin, however their strength and compliance were more like that of silicone rubber.

The above experiments were repeated in the presence of an artificially created hole in the fetal membrane to test the sealant ability of these compositions in the presence of saline. Briefly, the second set of experiments was carried out as follows. A cylindrical vessel 10-cm in diameter and 10-cm tall was completely filled with saline. Freshly harvested human fetal membranes were stretched (draped) over the open mouth of the cylindrical vessel, with the fetal surface facing the saline. The membranes were held firmly over the mouth of the vessel by a rubber band. The fetal side of the membrane was continuously bathed by the saline contained in the cylindrical vessel. The maternal surface of the membrane, to which LVPS and HVPS were being applied for the purpose of this experiment, was kept wet by continuous irrigation with saline. A forcep tip was used to perforate the fetal membrane stretched over the mouth of the cylindrical vessel. Thus, irregularly shaped defects were created in the fetal membrane ranging in size from 1 mm to approximately 8 mm. The size of the defect was purposefully varied to assess the ability of the LVPS and HVPS to seal small and large defects. LVPS and HVPS primer and/or sealant and/or light treatment were applied according to the four techniques a–d as described above.

The results showed that both LVPS and HPVS were very capable in sealing these rents. HPVS was clearly superior in sealing larger rents. This superiority was due to its greater viscosity, which allowed it to bridge the larger rents with greater ease. For both LVPS and HVPS, immediately after polymerization with the light wand the cylindrical vessel could be turned upside down. The fetal membrane would bulge slightly due to a pressure of approximately 100 mm $H_2O$, but no leakage of saline from the vessel was ever observed regardless of the size of the sealed rent. Pressures higher than 100 mm $H_2O$ were not evaluated.

Inspection of the fetal side of the sealed membrane revealed that, in the cases of larger rents, an icicle-like protrusion of polymerized compound (approximately 10 mm long) formed on the side of the membrane opposite to the polymer application site. With further experimentation it was discovered that the formation of this icicle-like protrusion could be minimized or completely avoided by application of polymerizing light concurrently rather than subsequent to sealant application.

The results of these sets of experiments show that both LVPS and HVPS were clearly effective in sealing rents in human chorioamniotic membrane.

EXAMPLE 2

Application of Intrauterine Polymeric Compositions in Primates

A hydrogel composition may be applied to the lower uterine segment and cervix of a pregnant primate, such as a baboon or human, as follows. In humans, rupture of amniotic membranes is diagnosed by detection of fetal hair, Nitrazine positive fluid, and presence of ferning in the vagina. The subject is positioned to assure that the cervix (1) is the uppermost structure of the uterus (dorsal lithotomy position and deep Trandelenburg position). See FIG. 1. The vagina and cervix are thoroughly cleaned with a neomycin containing solution under direct vision.

Figure 2:
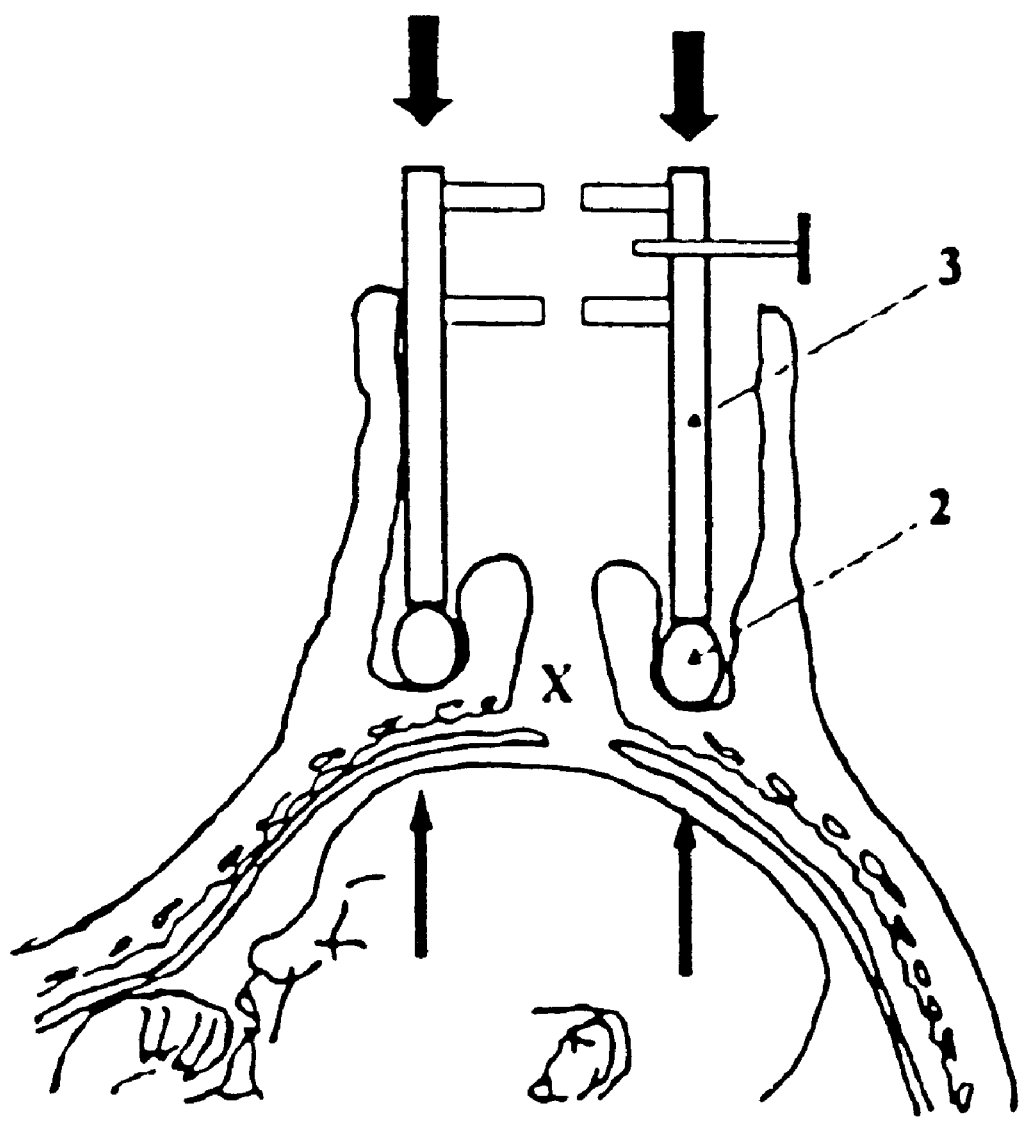

A donut shaped pliable device (2) is placed around the cervix and used to apply pressure against the fetal head with the help of a cylindrical non-pliable extension (3). Thus, a confined space (X) delimited by the cervix and fetal membrane covered fetal head will be created. See FIG. 2.

Figure 3:
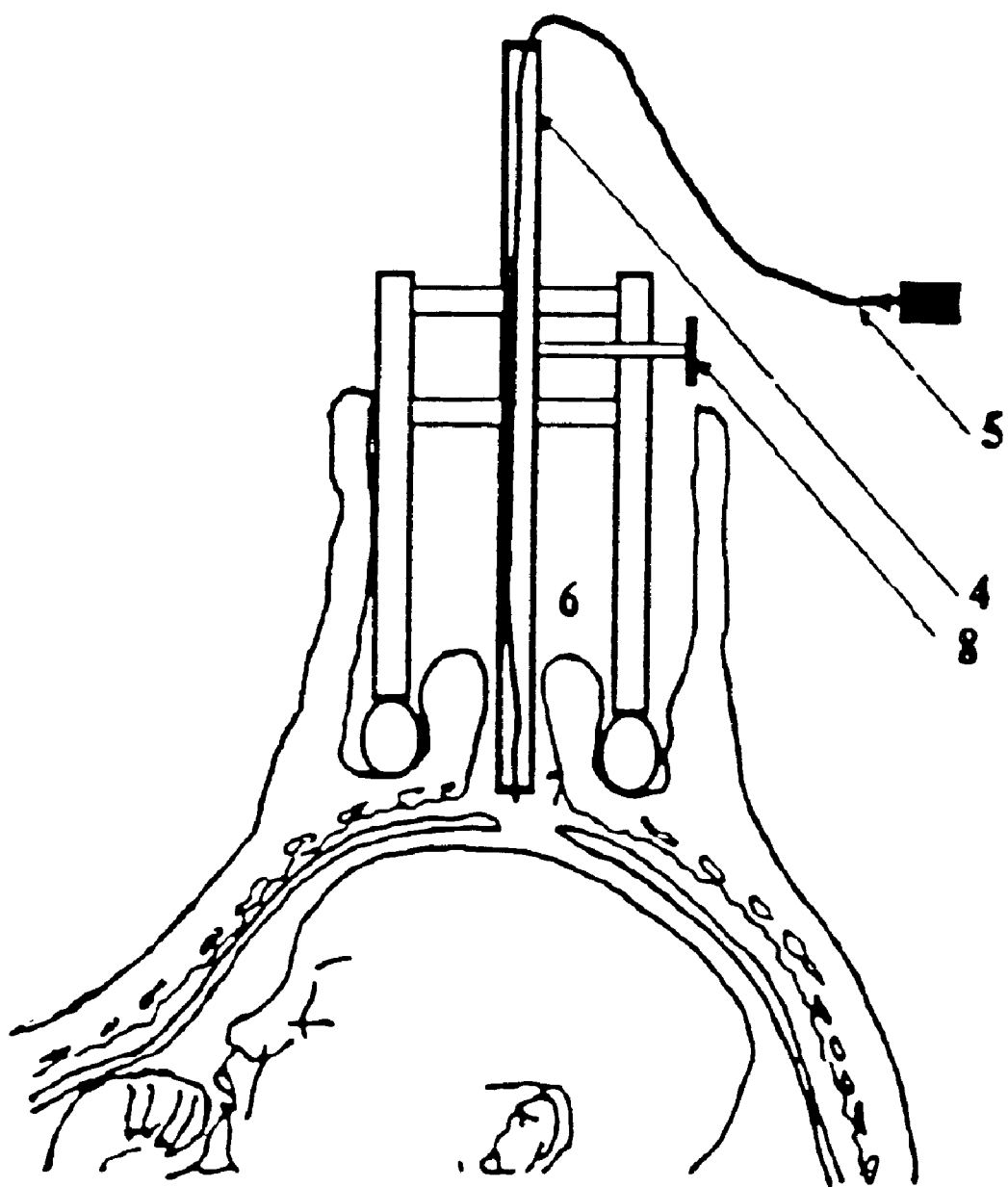

A rigid thin walled tube (4) containing a hysteroscope (5) is then advanced through the cylindrical device (3) and into the external cervical opening (6). Continuous visualization through the hysteroscope permits advancement of this rigid tube to the level of internal cervical os (7) and the depth of insertion may be measured and recorded. See FIG. 3.

The rigid thin walled tube is then fixed in place by a positioning fixation screw (8) located on the cylindrical non-pliable extension (3). See FIG. 3. The hysteroscope (5) is then removed from rigid thin walled tube (4).

Figure 4:
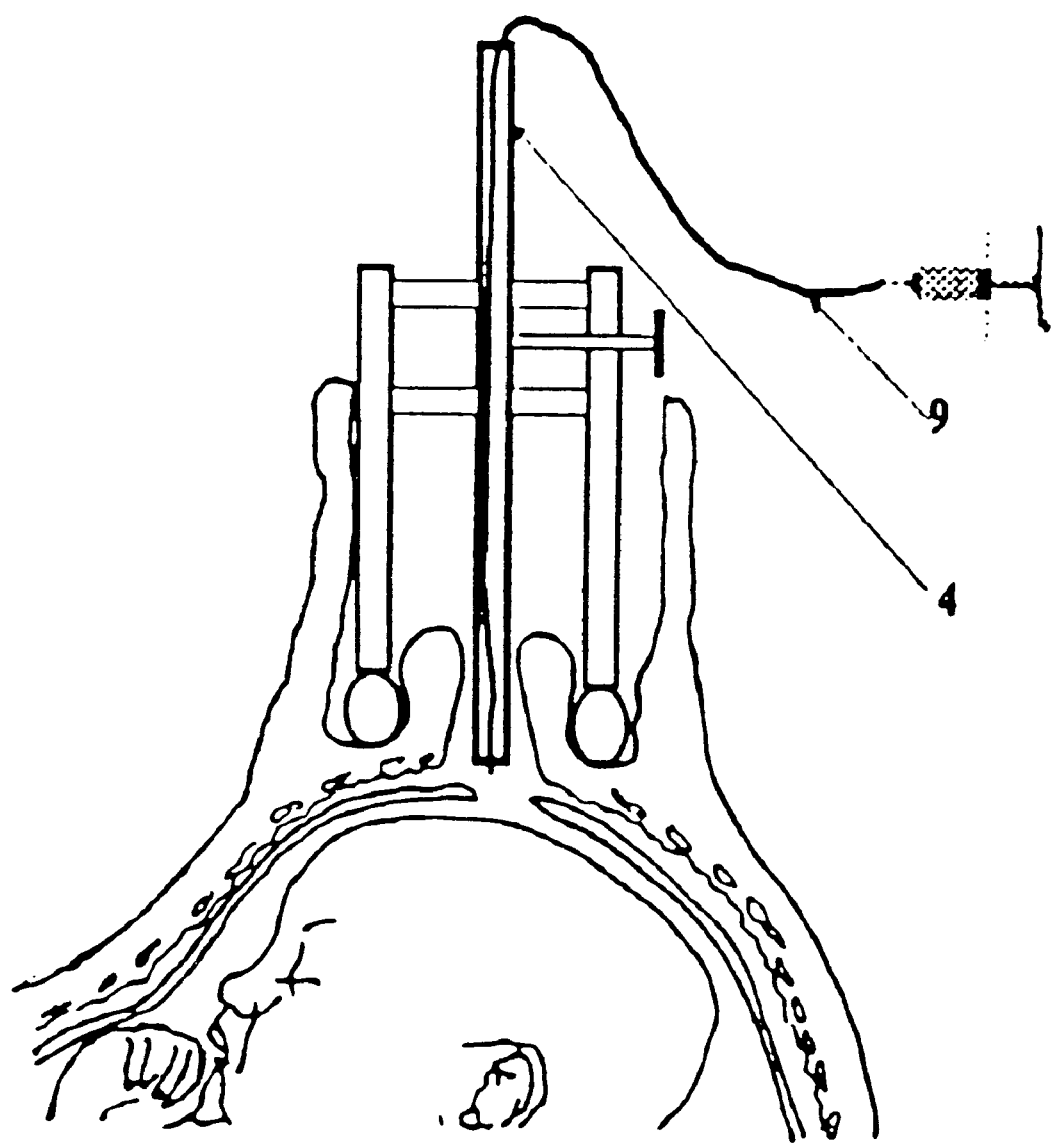

An irrigation catheter (9) is advanced through the rigid thin walled tube (4) to the previously determined depth of the internal cervical os. The lower uterine segment immediately adjacent to the internal cervical opening is irrigated through the irragation catheter (9) with a neomycin containing solution. See FIG. 4. The irrigation catheter (9) is then removed from the rigid thin walled tube (4).

Figure 5:
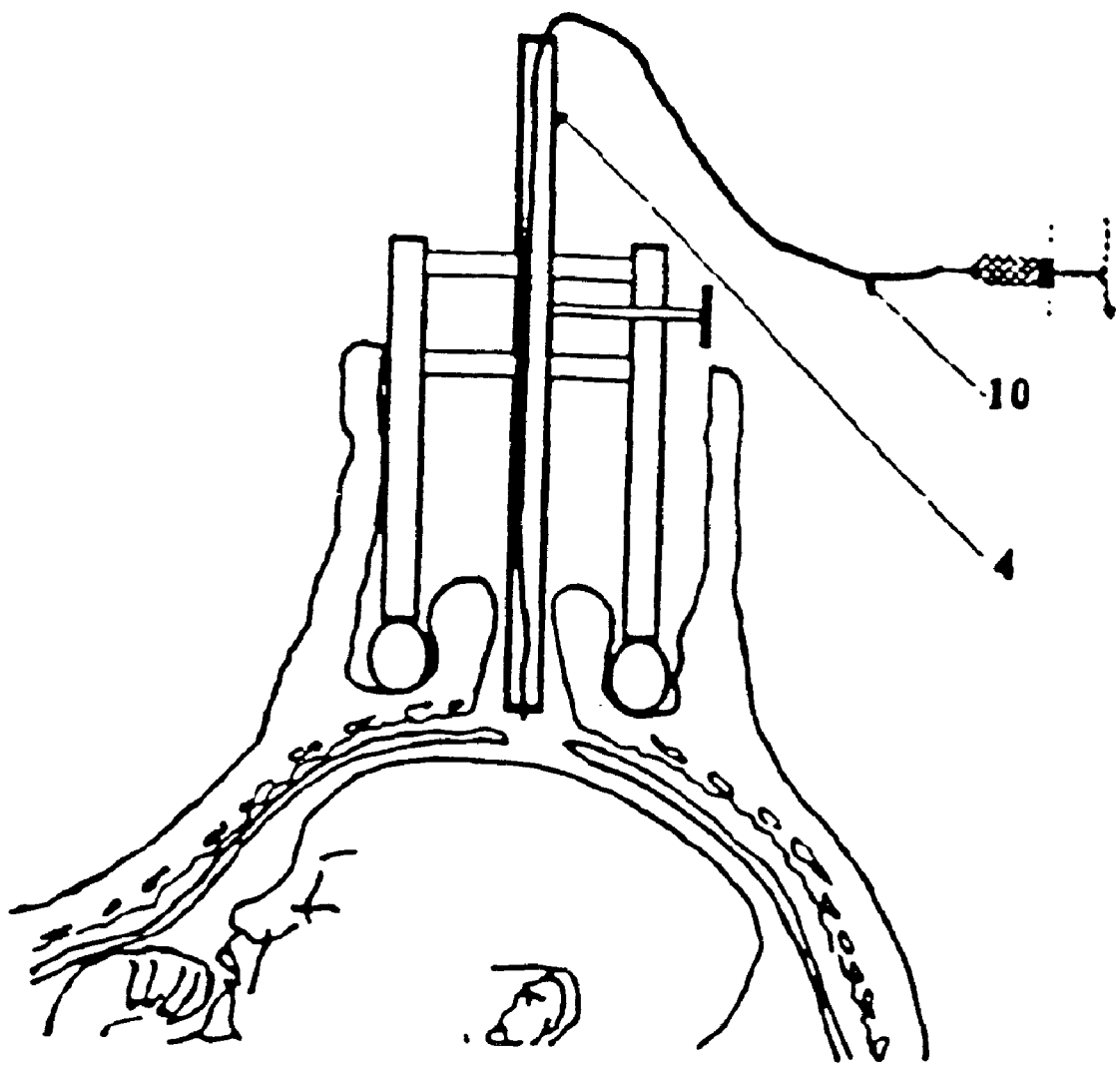

A suction catheter (10) is then advanced through the rigid thin walled tube (4) to the previously determined depth of the internal cervical os. Excess fluid is removed from the area of internal os by applying gentle suction via the suction catheter (10). See FIG. 5. The suction catheter is then removed.

If the polymerizable solution being used is formed from a set of multiple components (for example, the Primer and Sealant solutions of Focal Gel [Focal, Lexington, Mass.]), infusion of the components may occur via different catheters, as follows.

Figure 6:
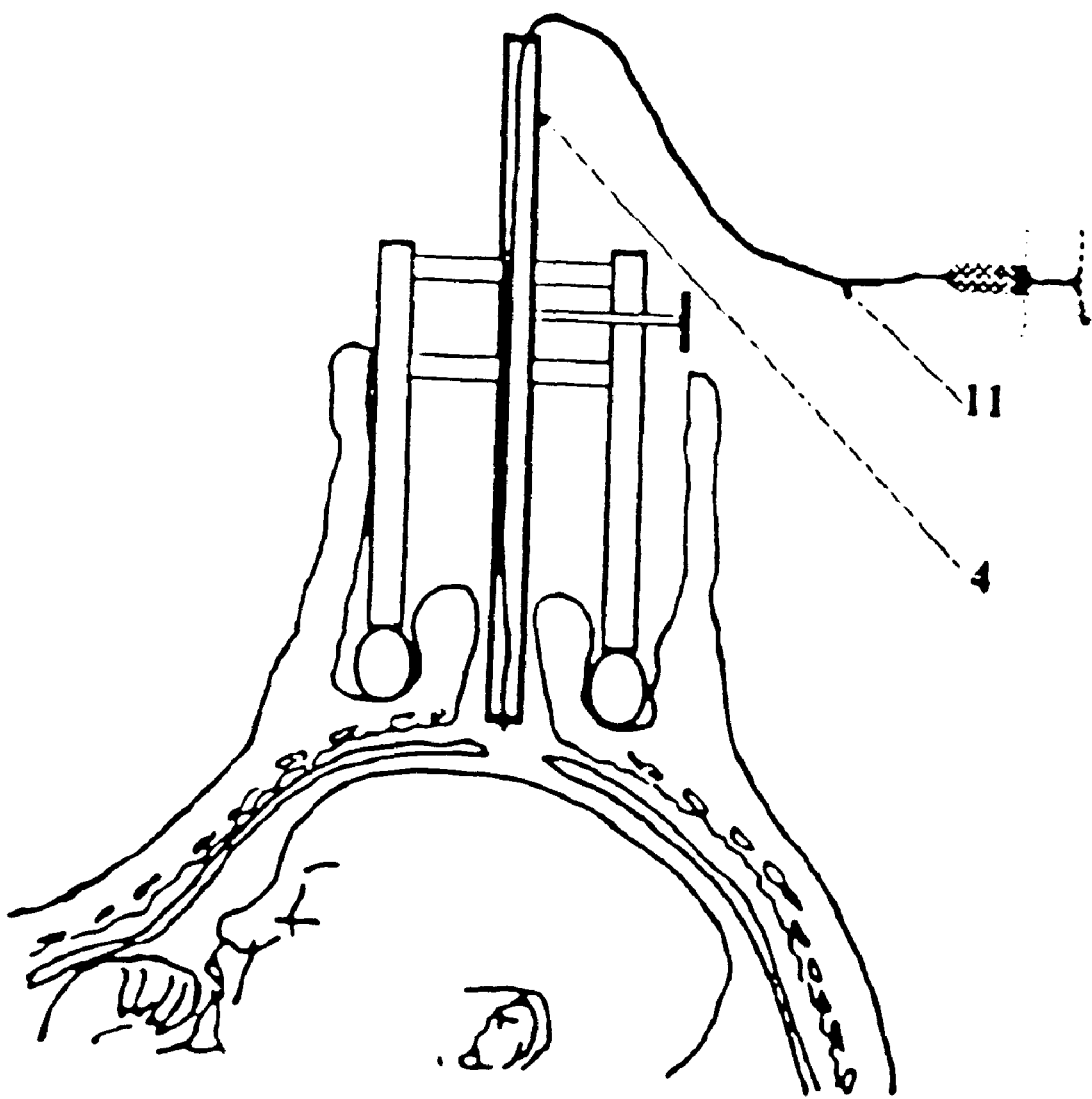

A primer infusion catheter (11) is then advanced through the rigid thin walled tube (4) to the previously determined depth of the internal cervical os. A Primer Solution is infused through the primer infusion catheter (11). See FIG. 6. Subsequently the primer infusion catheter (11) is removed from the thin walled tube (4). A new suction catheter (10) is then advanced once again through the rigid thin walled tube (4) to the previously determined depth of the internal cervical os. Excess Primer Solution is removed from the area of internal os by applying gentle suction via the suction catheter (10). The suction catheter is then removed.

Figure 7:
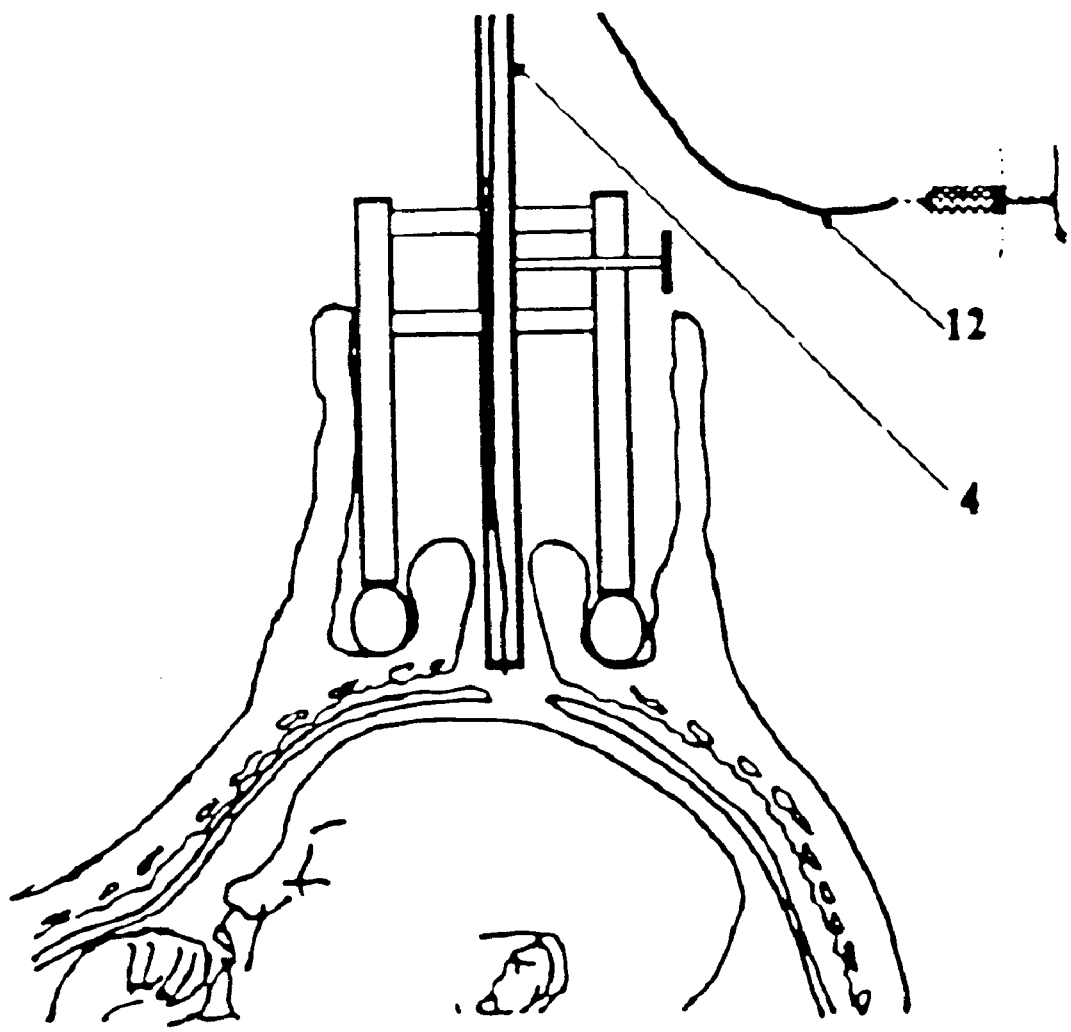

A sealant infusion catheter (12) is then advanced through the rigid thin walled tube (4) to the previously determined depth of the internal cervical os. A Sealant Solution is infused through the sealant infusion catheter (12). See FIG. 7. Subsequently the sealant infusion catheter (12) is removed from the rigid thin walled tube (4).

A polymerizable solution containing more than two components may require use of additional infusion catheters, while a polymerizable solution that is applied as a single solution only requires use of one infusion catheter.

Figure 8:
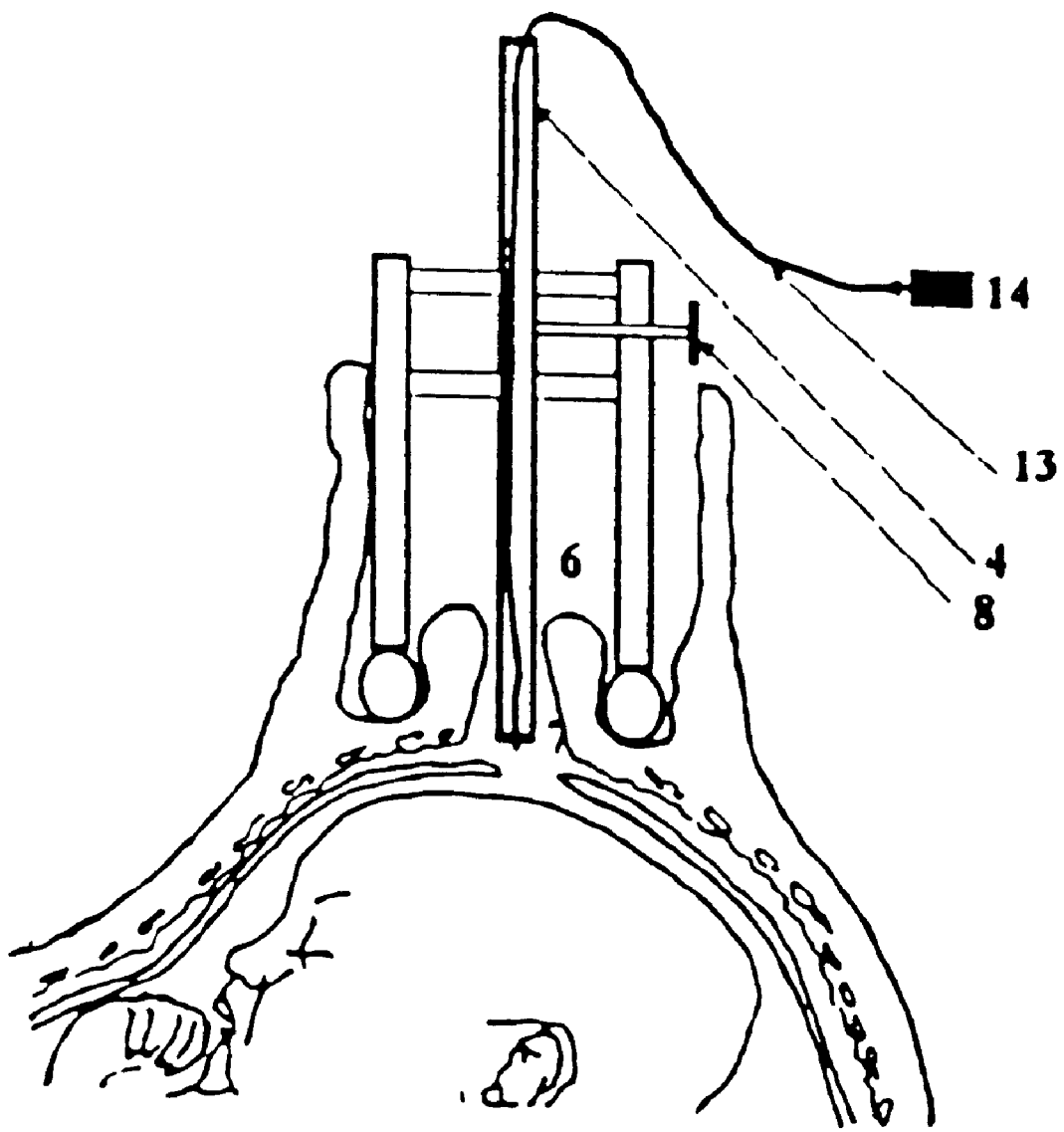

The hysteroscope and fiber-optic light guide (13) is then advanced through the rigid thin walled tube (4) until the surface of the sealant is visualized. The rigid thin walled tube (4), hysteroscope (5) and fiber-optic light guide (13) are withdrawn slightly, so that none of these structures contact the sealant, and polymerizing visible light from a light source (14) is applied. See FIG. 8.

The primer and sealant application steps and the subsequent light polymerization step may be repeated to form a polymeric plug of the same or different composition at the internal os of the cervix. The procedure may also be repeated to deliver and cross-link a substance of the same or different composition in the cervical canal and again in the vagina surrounding the cervix.

After application of the polymeric composition(s) is complete, all devices are removed from the vagina and the subject is observed for amniotic fluid leakage.

All steps are ideally performed under ultrasonic and or fiber-optic visualization.

The physical support and biocompatibility properties of the polymeric compositions are confirmed in baboons by injecting baboons at various stages of gestation with one or more types of polymeric compositions and monitoring the progress of gestation in the baboons.

Numerous modifications and variations of the above-described invention are expected to occur to those of skill in the art. Accordingly, only such limitations as appear in the appended claims should be placed thereon.

What is claimed are:

1. A method for reducing the incidence of preterm birth comprising the steps of:
   administering a hydrogel into the lower uterine segment of the uterus of a pregnant female in a manner that provides support to the chorioamniotic membrane, and polymerizing said hydrogel to reduce the incidence of preterm birth.

2. The method of claim 1 wherein said hydrogel adheres to the chorioamniotic membrane.

3. The method of claim 1 wherein said hydrogel has an elongation at rupture similar to or greater than the elongation at rupture of chorioamniotic membrane.

4. The method of claim 1 wherein the force required to rupture said hydrogel is similar to or greater than the force required to rupture chorioamniotic membrane.

5. The method of claim 1 wherein said hydrogel is characterized by an elongation at rupture, elastic modulus, tensile stress and tensile modulus that provides sufficient physical support to reduce stretching of the chorioamniotic membrane into the uterine cervix during pregnancy.

6. The method of claim 1 wherein said hydrogel forms a physical barrier preventing migration of vaginal microbes into the uterus.

7. The method of claim 1 further comprising a second polymeric composition located intracervically.

8. The method of claim 7 further comprising a third polymeric composition located in the vaginal portion of the cervix.

9. The method of claim 1 wherein said second and third polymeric compositions are the same as or different from the hydrogel.

10. The method of claim 8 wherein one of said hydrogel, or second or third polymeric compositions can release therapeutic amounts of pharmaceutical agents into the uterine and cervical area.

11. The method of claim 8 wherein one of said hydrogel, or second or third polymeric compositions comprises microspheres comprising a pharmaceutical agent.

12. The method of claim 1 wherein the pregnancy is prolonged.

13. The method of claim 1 wherein leakage of amniotic fluid is prevented.

14. The method of claim 1 wherein the female is suffering from premature labor.

15. The method of claim 1 wherein the female is suffering from premature rupture of fetal chorioamniotic membrane (PROM).

16. The method of claim 1 wherein the female is at risk of preterm labor.

17. The method of claim 16 wherein the female has signs of risk of preterm labor selected from the group consisting of high levels of oncofetal fibronectin, documented high proteolytic activity, signs of pre-term cervical softening or ripening, a significantly shorter cervix, a prior history of cervical incompetence, cervical funneling, a prior history of preterm birth, and a prior history of PROM.

18. The method of claim 1 wherein said polymeric composition is a hydrogel.

19. The method of claim 1 wherein said polymerizable composition further comprises a pharmaceutical agent.

20. The method of claim 1 further comprising the steps of administering a polymerizable composition into the cervix of a pregnant female, and polymerizing said composition.

21. The method of claim 1 wherein said hydrogel is present adjacent to the chorioamniotic membrane.

* * * * *